(12) United States Patent
Kulkarni et al.

(10) Patent No.: US 7,491,828 B2
(45) Date of Patent: Feb. 17, 2009

(54) LIQUID PHASE PROCESS FOR THE SYNTHESIS OF ANNULATED PYRIDINES OVER MOLECULAR SIEVE CATALYSTS

(75) Inventors: Shivanand J. Kulkarni, Hyderabad (IN); Veera V. Krishna Kandepi, Hyderabad (IN); Narender Nama, Hyderabad (IN); Kondapuram V. Raghavan, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 235 days.

(21) Appl. No.: 11/027,484

(22) Filed: Dec. 30, 2004

(65) Prior Publication Data

US 2006/0149068 A1    Jul. 6, 2006

(51) Int. Cl.
*C07D 213/08*    (2006.01)
*C07D 213/14*    (2006.01)

(52) U.S. Cl. .................................................. 546/250
(58) Field of Classification Search .................. 546/250
See application file for complete search history.

(56) References Cited

U.S. PATENT DOCUMENTS 4,006,236 A    2/1977  Schrider 4,220,783 A    9/1980  Chang et al.
5,952,258 A *  9/1999  Saitoh et al. .................. 502/61

FOREIGN PATENT DOCUMENTS

WO    WO 02/079166    10/2002

OTHER PUBLICATIONS

Kulkarni et al., Studies in surface science and catalysis, 2004, 154C, pp. 2781-2787.*
Tchitchibabin: "Sur les reactions de condensation des aldehydes et cetones avec l'ammoniaque en bases pyridiques. Condensations avec les cetones cycliques" Bull. Soc. Chim. Fr., vol. 6, 1939, pp. 522-533, SP09052662, p. 524.
International Search Report for PCT/IN2004/000442, dated Aug. 30, 2005.
Thummel, Randolph P., et al., "Preparation and Properties of Annelated Pyridines", J. Org. Chem., 1977, vol. 42, No. 16, pp. 2742-2747.

* cited by examiner

*Primary Examiner*—Janet L Andres
*Assistant Examiner*—Niloofar Rahmani
(74) *Attorney, Agent, or Firm*—Darby & Darby P.C.

(57) ABSTRACT

The present invention relates to a process for producing annulated pyridines by reacting cyclic ketone, aldehyde and ammonia in presence of molecular sieve type catalysts in an environmentally friendly, economical and highly selective heterogeneous method.

13 Claims, No Drawings

US 7,491,828 B2

LIQUID PHASE PROCESS FOR THE SYNTHESIS OF ANNULATED PYRIDINES OVER MOLECULAR SIEVE CATALYSTS

FIELD OF THE INVENTION

The present invention relates to an improved liquid phase process for the synthesis of annulated pyridines (fused pyridines) over molecular sieve catalysts. In particular, the present invention provides a process for producing 1,2,3,4,5,6,7,8-octahydroacridine and octahydrophenanthridine by reacting cyclohexanone and formaldehyde with ammonia in liquid phase over molecular sieve catalysts with high yields and selectivity. The present invention provides a non-corrosive, eco-friendly process, where the life time of the catalyst is longer, it can be recycled and reused for many times, less wastage of compounds (e.g. high atom selectivity) and high selectivity of the products.

BACKGROUND OF THE INVENTION

Annulated pyridines like 9-amino-5,6,7,8tetrahydroacridine (tacrine) are drug or drug intermediates for various diseases like Alzheimer's disease, which is the most common cause of dementia in old people. Many methods of producing pyridine bases are known, for example reacting an aliphatic aldehyde and/or ketone with ammonia in gaseous phase using a solid acid catalyst such as amorphous aluminosilicate and the like (Japanese Patent Application Kokai (Laid-open) No.63176/76, Japanese Patent Publication No.3 41546/71 and 32790/69). Crystalline aluminosilicate, called zeolite is used as the catalyst for producing pyridine bases from an aliphatic aldehyde and ketone (or formaldehyde) and ammonia (U.S. Pat. No. 4,220,783, Japanese Patent Application Kokai (Laid-open) No.38362/85, Indian Patent Nos. IN-185390, IN-185654). According to these processes one ring pyridine compounds are produced but fused ring heterocyclics have not yet been reported over zeolite molecular sieve catalysts. Increasing applications of these annelated pyridines demand an eco-friendly, economical and free handling process. The present invention provides an eco-friendly and economical process for synthesis of a variety of these compounds.

The synthesis of octahydroacridine and octahydrophenanthridine was carried out using homogenous catalyst like ammonium acetate and ammonium hydroxide but the yield were lower than 54% and usual disadvantages of homogenous catalysis were observed (J. Org. Chem. 42 (No. 16), p 2742 (1977). The synthesis of octahydrophenanthridine was also carried out using p-tolune sulfonic acid and $POCl_3$ as homogenous catalyst(s) from 2(1-cyclohexenyl)-cyclohexanone and $RCONH_2$ (U.S. Pat. No. 4,006,236 (1977). The reaction time is longer, 10-24 hrs and the catalyst can not be reused and silica-alumina, chronia or magnesia catalyst(s) at comparatively high reaction temperature 180-425° C. in vapour phase with low selectivity for a particular product. Our process using molecular sieve is eco-friendly, catalyst is reusable, separation is easy and selective.

OBJECTS OF THE INVENTION

The main objective of the present invention is to provide process for the synthesis of octahydroacridine, octahydrophenanthridine and their derivatives, by using (modified or unmodified) zeolite or molecular sieve catalyst, which is an eco-friendly heterogeneous catalytic method.

Another objective of the invention is to improve yield and selectivity of the product.

SUMMARY OF THE INVENTION

The present invention provides an improved process for the synthesis of annulated pyridines over a molecular sieve catalyst, the process comprising reacting a cyclic ketone having 5-8 carbons and an aliphatic aldehyde of the formula $R^1CHO$ wherein $R^1$ is hydrogen or an alkyl group having 1 to 4 carbon atoms, with ammonia in an organic solvent in presence of a zeolite-type molecular sieve or heterogeneous catalyst, separating the catalyst to obtain the desired product.

In one embodiment of the invention, the cyclic ketone is cyclohexanone.

In another embodiment of the invention, the aliphatic aldehyde is selected from the group consisting of formaldehyde, acetaldehyde, propionaldehyde, and butyraldehyde.

In another embodiment of the invention, the molar ratio of cyclic ketone:aliphatic aldehyde-ammonia is in the range of 1:10.5 to 5.0.

In another embodiment of the invention, the reaction is carried out in liquid phase with a molar ratio of ammonia to cyclic ketone in the range of 0.5 to 5.0 and at a temperature in the range of 100° C. to 250° C., for a period of 4-8 hrs.

In another embodiment of the invention, the reaction is carried out in an autoclave.

In another embodiment of the invention, the organic solvent is selected from the group consisting of methanol, ethanol, isopropanol, acetonitrile and acetone, preferably methanol.

In another embodiment of the invention, the catalyst is selected from the group consisting of H-beta (Hβ), HY, HZSM-5 having a Si/Al ratio in the range of 40-300, H-mordenite, montmorillonite and $SiO_2$—$Al_2O_3$ zeolite and molecular sieve H—AlMCM-41.

In another embodiment of the invention, the ratio of Si to Al in the zeolite catalyst is in the range of 2.5-300.

In another embodiment of the invention, the catalyst is reusable.

In another embodiment of the invention, the annulated prydine obtained comprises 1,2,3,4,7,8,9,10-otahydrophenanthridine, 1,2,3,4,5,6,7,8-octahydroacridine, 6-methyl octabydrophenanthridine, 6-ethyloctahydrophananthridine and 6-propyloctahydrophenanthridine.

DETAILED DESCRIPTION OF THE INVENTION

The present invention provides a process for the preparation of octahydroacridine of the formula number 1 to 9 below from cyclic ketones and aliphatic aldehyde with ammonia over molecular sieves. These annelated pyridines, like 9-amino-5,6,7,8-tetrahydroacridine (tacrine), are drug molecules or drug intermediates for various diseases like Alzheimer's disease, which is the most common cause of dementia in old people.

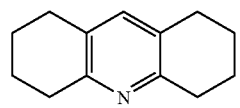 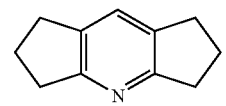

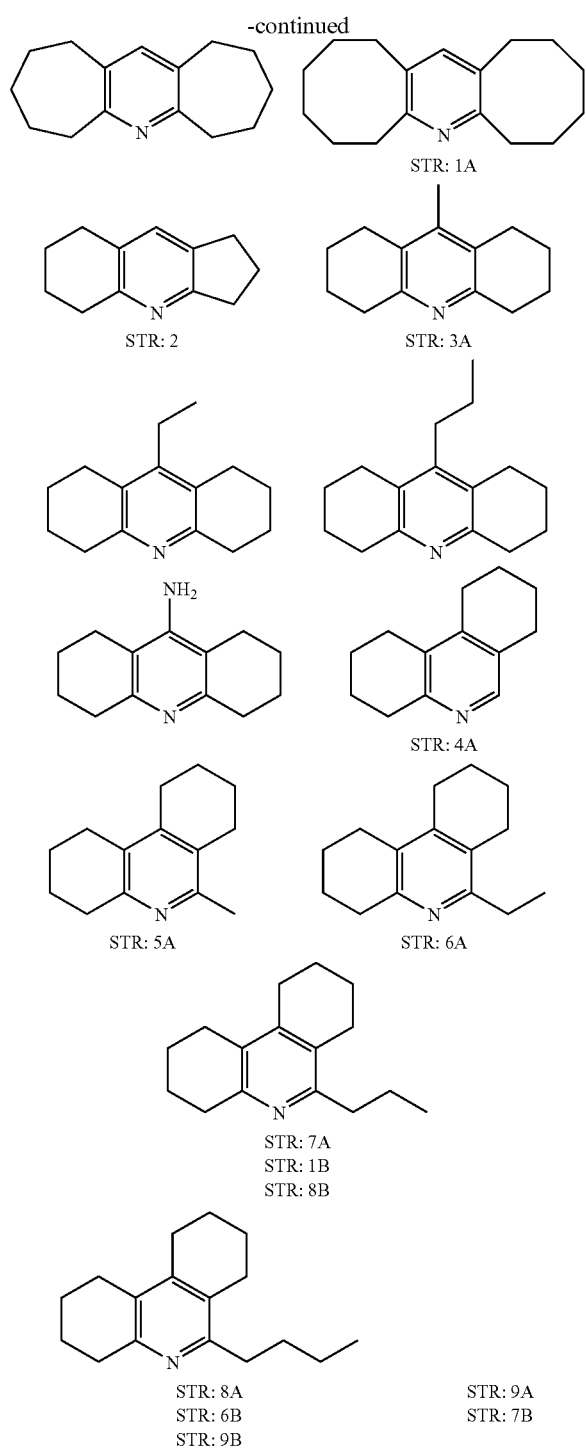

Salient Features of the Process (a) The present invention provides a process that comprises of environmentally clean and economical technology and enables reusability of the catalyst;
(b) The process provides an eco-friendly method with high selectivity towards the product.
(c) The method provides a selective heterogeneous catalyst with longer life.
(d) This method provides a route, wherein the kind and composition of annulated pyridines can be varied by varying the starting materials,
(e) It also provides an efficient, economical method for synthesizing octahydroacridine and octahydrophenanthridine from cyclohexatone and formaldehyde with ammonia over various molecular sieve catalysts.

The present invention relates to a process for producing annulated pyridines by reacting a cyclic ketone and an aliphatic aldehyde with ammonia in liquid phase in the presence of a commercial or synthesized catalyst.

The aliphatic cyclic ketone used in the present invention includes cyclohexanone, cyclopentanone, cycloheptanone and cyclooctanone. The aliphatic aldehyde includes formaldehyde, acetaldehyde propionaldehyde, butyraldehyde and formamide. The combination of different cyclic ketones and aliphatic aldehydes as starting materials determines the main compounds of the annulated pyridine to be produced. Typical examples are given in the Table 1.

TABLE 1

| Aldehyde | Ketone | Main products formed |
|---|---|---|
| Formaldehyde | Cyclohexanone | Octahydroacridine, Octahydrophenanthridine |
| Acetaldehyde | Cyclohexanone | 6-methyloctahydrophenanthridine |
| Propionaldehyde | Cyclohexanone | 6-ethyloctahydrophenanthridine |
| Butyraldehyde | Cyclohexanone | 6-propyloctahydrophenanthridine |
| Valaraldehyde | Cyclohexanone | 6-butyloctahydrophenanthridine |
| Formaldehyde | Cyclopentanone | Bis-bicyclopentylpyridine |
| Formaldehyde | Cycloheptanone | Bis-bicycloheptylpyridine |

The reaction of the present invention may be conducted in a batch-mode in an autoclave, The reaction in batch-mode were carried out in Parr autoclave(600 mL) in the reaction temperature range of 100-250° C. under constant stirring (30-60 revolutions per min). The typical molar ratio of cyclohexanone:formaldehyde:$NH_3$ was 1:1:3 and 222 mL methanol was used as solvent. The autoclave time was 6 h.

A combination of cyclic ketone, aliphatic aldehyde and ammonia (or nitrogen source), for production of octahydroacridine and octahydrophenanthridine, was taken in the molar ratio of 1:1:0.5-5. The reaction can be effected without trouble or without much coking if the (liquid) starting materials contains water, methanol or the like solvent, Formaldehyde can be used in the form of formalin. The amount of coke deposited was less so higher yields of the products were obtained; in comparison with other commercial processes. The coke can be removed by heating the catalyst at 450° C. to 550° C.; for about 4-10 h.

The present invention is described below with reference to the following illustrative and non-limiting examples.

EXAMPLE 1

The reaction of cyclohexanone, formaldehyde and ammonia was carried out in an autoclave (600 ml) in presence of methanol as a solvent. Hβ (H-beta) was used as catalyst. The reaction was carried out in the temperature range of 100° C. to 215° C. for 6 h. The amount of catalyst was 2 g. The molar ratio of cyclohexanone:formaldehyde:ammonia was 1:1:3, The liquid: catalyst ratio was 104.8 by weight. In a typical experiment the reaction. (autoclavation) temperature was 150° C. The selectivities of octahydrophenainthridine were 50.2, 60.5, 44.8 and 32.2 percent at 53.0, 83.0, 97.7 and 98.7 percent conversions of cyclohexanone at 100°(4), 150°(14), 170°(20) and 215° C.(49 atm) reaction temperature respectively. The selectivities of octahydroacridine were 7.7, 21.7, 39.4 and 42.2 percent respectively. With the increase of the autoclavation temperature the autogeneous pressure increased. With increase of autoclavation temperature the conversion and selectivities for octahydroacridine increased while the selectivities for octahydrophenanthridine decreased. The other products were cyclohexamine and cyclohexanoneoxime. Under similar to the supercritical conditions and with the increase of reaction temperature, there is substantial increase of reactive collisions, miscibility is increased, the mass transfer and heat transfer effects are enhanced resulting into increased yield of preferably of octahydroacridine using active zeolite catalyst.

EXAMPLE 2

The reaction was carried out as explained in Example 1, with HZSM-5 catalyst. The autoclavation temperature was 150° C. The selectivities of octahydrophenanthridine and octahydroacridine were 54.6 and 28.8 percent at 80.3 percent conversion of cyclohexanone, over HZSM-5 ($SiO_2/Al_2O_3=40$).

EXAMPLE 3

Reaction was carried out as described in Example 1 with HY zeolite as a catalyst, The selectivities for octahydrophenanthridine and octahydroacridine were 62.3% and 31.2% at 57.2% conversion of cyclohexanone over HY zeolite. Autoclavation temperature was 150° C.

EXAMPLE 4

The reaction was carried out as described in Example 1, with H-mordenite as a catalyst. The selectivities of octahydrophenanthridine and octahydroacridine were 70.8% 19.8% at 89.1% conversion of cyclohexanone over H-mordenite zeolite. The autoclavation temperature was 150° C.

EXAMPLE 5

The reaction of cyclohexanone, formaldehyde and ammonia was carried out as described in Example 1, with EMCM-41 ($SiO_2/Al_2O_3=30$) as a catalyst. The selectivities of octahydrophenanthridine and octahydroacridine were 64.6% and 24.1% at 91.6% conversion of cyclohexanone over HMCM-41 mesoporons molecular sieve catalyst. The autoclavation temperature was 150° C.

EXAMPLE 6

The reaction of cyclohexanone, formaldehyde and ammonia was carried out as described in Example 1, with HZSM-5 ($SiO_2/Al_2O_3=40-280$) as a catalyst. The selectivities of octahydrophenanthridine were 40.4%, 48.7% and 54.6% at 71.3%, 81.0% and 80.3% conversions of cyclohexanone over HZSM-5 ($SiO_2/Al_2O_3=280$) HZSM-5 (150) and HZSM-5 (40) zeolites respectively. The selectivities of octahydroacridine were 10.6%, 18.4% and 28.8% respectively. The autoclavation temperature was 150° C.

EXAMPLE 7

The reactions of cyclohexanone, formaldehyde and ammonia were carried out as described in example 1, with H-beta (1-4 gm) as a catalyst. The selectivities of octahydropheaanthridine were 38.4, 60.6 and 73.6 percent at 75.6, 83.0 and 94.4 percent conversions of cyclohexaaone over H-beta(1 gm), H-beta(2 gm) and H-beta(4 gm) zeolites respectively. The selectivities of octahydroacridine were 12.6, 21.7 and 19.7 percent respectively. The autoclavation temperature was 150° C.

EXAMPLE 8

The reactions of cyclohexanone, formaldehyde and ammonia were carried out as described in example 1, with H-beta (2 gm) as a catalyst. The effect of solvent has been studied. The amount of solvent was 222 ml. The selectivities of octahydrophenanthridine were 60.6, 44.1, 37.7, 20.4 and 8.4 percent at 83.0, 84.4, 77.7, 76.4 and 83.6 percent conversions of cyclohexanone for methanol (p=14 atm), ethanol (p=11 atm), acetonitrile (p=10 atm) and acetone (p=13 atm) as a solvent respectively. The corresponding selectivities for octahydroacridine were 21.7, 38.3, 40.1, 12.9 and 2.2 percent respectively. The molar ratio of cyclohexanone:formaldehyde:ammonia was 1:1:3.

EXAMPLE 9

The reaction of cyclohexanione, formaldehyde and ammonia was carried out as described in example 1 with H-beta (2 gm) as a catalyst, the reaction was carried out at 228° C. autoclavation (reaction) temperature and pressure was 64 atm. The reaction conditions are similar to the supercritical conditions for 6 hr using methanol (220 ml) as a solvent. The selectivities for octahydrophenanthridine and octahydroacridine were 23.9 and 40.6 percent at 98.4 percent conversion of cyclohexanone.

EXAMPLE 10

The reactions of cyclohexanone, aliphatic aldehyde and ammonia were carried out as described in example 1, with H-beta (2 gm) as a catalyst. The reaction was carried out at 150° C. using methanol (220 ml) as a solvent and the molar ratio of cyclohexanone:aliphatic aldehyde:ammonia was 1:1:3. The selectivities for 6-methyloctahydrophenanthridine, 6-ethyloctahydrophenanthridine, 6-propyloctahydrophananthridine and 6-butyloctahydrophenanthridine were 80.9, 45.4, 63.2 and 27.7 percent at 97.0, 90.0, 96.4 and 93.5 percent conversions of cyclohexanone respectively.

EXAMPLE 11

The reactions of cyclohexanone, acetaldehyde and ammonia were carried out as described in example 1 using methanol (220 ml) as a solvent; by varying the various zeolites as catalysts. The reactions were carried out at 150° C. and the molar ratio of cyclohexanone: acetaldehyde:ammonia was 1:1:3. The selectivities for 6-methylphenanthridine were 80.9, 39.5, 54.3, 32.2, 56.9, 79.8, 47.1, 48.4 percent at 97.0, 84.9, 94.9, 87.3, 96.7, 95.8, 87.7 and 90.3 percent conversions of cyclohexanone for H-beta, HZSM-5 ($SiO_2/Al_2O_3=280$), HZSM-5(40), HY, H-mordenite, HMCM-41($SiO_2/Al_2O_3=30$), Montmorillonite (K-10) and $SiO_2$—$Al_2O_3$ (amorphous) catalysts respectively.

EXAMPLE 12

The reactions of cyclohexanone, propionaldehyde and ammonia were carried out as described in example 1, using methanol (220 ml) as a solvent; by varying the particularly zeolites as catalysts. The reactions were carried out at 150° C. and the molar ratio of cyclohexanone:propionaldehyde:ammonia was 1:1:3. The selectivities for 6-ethyloctahydrophenanthridine were 45.4, 41.8, 37.7, 35.3, 39.0, 43.4, 41.5, 51.3, 28.4 percent at 90.0, 77.4, 83.3, 75.5, 80.0, 90.7, 78.2, 92.8 and 89.1 percent conversions of cyclohexanone using H-beta, HZSM-5($SiO_2/Al_2O_3$=300), HZSM-5($SiO_2/Al_2O_3$=150), HZSM-5($SiO_2/Al_2O_3$=40), HY, H-mordenite, HMCM-41 ($SiO_2/Al_2O_3$=30), montmorillonite and $SiO_2$—$Al_2O_3$ (amorphous) catalysts respectively.

EXAMPLE 13

The reactions of cyclohexanone, butyraldehyde and ammonia were carried out as described in example 1, using methanol (220 ml) as a solvent by varying particularly various zeolites (2 gm) as catalysts. The reactions were carried out at 150° C. and the molar ratio of cyclohexanone:butyraldehyde:ammonia was 1:1:3. The selectivities for 6-propylphenanthridine were 46.8, 47.0, 36.5, 63.2 and 42.1 percent at 95.8, 95.7, 91.1, 96.4 and 95.6 percent conversions of cyclohexanone using HZSM-5 ($SiO_2/Al_2O_3$=150), HZSM-5 (40), HY, H-mordenite and NaY zeolite respectively, The main by-product was cyclohexaneoxime.

We claim:

1. A process for the synthesis of annulated pyridines over a molecular sieve catalyst, the process comprising:
   (a) reacting a cyclic ketone having 5-8 carbons and an aliphatic aldehyde of the formula $R^1CHO$, wherein $R^1$ is hydrogen or an alkyl group having 1 to 4 carbon atoms, with ammonia in an organic solvent in the presence of a zeolite-type molecular sieve or heterogeneous catalyst; and
   (b) separating the catalyst to obtain the desired product.

2. A process as claimed in claim 1 wherein the cyclic ketone is selected from the group consisting of cyclohexanone, cyclopentanone, cycloheptanone and cyclooctanone.

3. A process as claimed in claim 1 wherein the aliphatic aldehyde is selected from the group consisting of formaldehyde, acetaldehyde, propionaldehyde, butyraldehyde and formamide.

4. A process as claimed in claim 1 wherein the cyclic ketone is cyclohexanone.

5. A process as claimed in claim 1 wherein the molar ratio of cyclic ketone:aliphatic aldehyde:ammonia is in the rage of 1:1:0.5 to 1:1:5.0.

6. A process as claimed in claim 1 wherein the reaction is carried out in liquid phase with a molar ratio of ammonia to cyclic ketone in the range of 0.5 to 5.0 and at a temperature in the range of 100°C. to 250°C., for a period of 4-8 hrs.

7. A process as claimed in claim 1 wherein the reaction is carried out in an autoclave.

8. A process as claimed in claim 1 wherein the organic solvent is selected from the group consisting of methanol, ethanol, isopropanol, acetonitrile and acetone.

9. A process as claimed in claim 1 wherein the solvent is methanol.

10. A process as claimed in claim 1 wherein the catalyst is selected from the group consisting of H-beta (Hβ), HY, HZSM-5 having a Si/Al ratio in the range of 40-300, H-mordenite, montmorillonite and $SiO_2$-$Al_2O_3$ zeolite and molecular sieve H-AlMCM-41.

11. A process as claimed in claim 1 wherein the ratio of Si to Al in the zeolite catalyst is in the range of 2.5-300.

12. A process as claimed in claim 1 wherein the catalyst is reusable.

13. A process as claimed in claim 1 wherein the annulated prydine obtained comprises 1,2,3,4,7,8,9,10-octahydrophenanthridine, 1,2,3,4,5,6,7,8-octahydroacridine, 6-methyl octahydrophenanthridine, 6-ethyloctahydrophananthridine and 6-propyloctahydrophenanthridine.

* * * * *